US008241334B2

(12) United States Patent
Butler et al.

(10) Patent No.: US 8,241,334 B2
(45) Date of Patent: Aug. 14, 2012

(54) SPINAL CROSS-CONNECTOR

(75) Inventors: Michael S. Butler, St. Charles, IL (US);
Kara A. Bucci, Palos Park, IL (US);
Brian D. Hartsell, Aurora, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 713 days.

(21) Appl. No.: 12/172,225

(22) Filed: Jul. 12, 2008

(65) Prior Publication Data
US 2009/0018586 A1 Jan. 15, 2009

Related U.S. Application Data

(60) Provisional application No. 60/959,338, filed on Jul. 13, 2007.

(51) Int. Cl.
*A61B 17/70* (2006.01)
(52) U.S. Cl. .......... 606/278; 606/251
(58) Field of Classification Search .......... 606/250, 606/270, 279, 86 A, 251, 253, 278, 277, 264, 606/286, 280, 308
See application file for complete search history.

(56) References Cited

U.S. PATENT DOCUMENTS

| | | | | |
|---|---|---|---|---|
| 5,667,526 | A | * | 9/1997 | Levin .................. 606/207 |
| 5,727,899 | A | | 3/1998 | Dobrovolny |
| 5,947,966 | A | * | 9/1999 | Drewry et al. .......... 606/252 |
| 6,017,306 | A | | 1/2000 | Bigliani et al. |
| 6,096,039 | A | * | 8/2000 | Stoltenberg et al. ...... 606/252 |
| 6,110,173 | A | * | 8/2000 | Thomas, Jr. ............ 606/252 |
| 6,123,482 | A | | 9/2000 | Keller |
| 6,132,430 | A | * | 10/2000 | Wagner .................. 606/264 |
| 6,171,311 | B1 | * | 1/2001 | Richelsoph ............. 606/252 |
| 6,238,396 | B1 | * | 5/2001 | Lombardo .............. 606/86 A |
| 6,311,586 | B1 | | 11/2001 | Hirse |
| 6,524,310 | B1 | | 2/2003 | Lombardo et al. |
| 6,616,664 | B2 | | 9/2003 | Walulik et al. |

(Continued)

OTHER PUBLICATIONS

Written Opinion of the International Searching Authority for PCT Application No. PCT/US2008/069899, mail date Sep. 8, 2008, 4 pages.

*Primary Examiner* — Pedro Philogene
(74) *Attorney, Agent, or Firm* — Foley & Lardner LLP

(57) ABSTRACT

A spinal cross-connector is configured for adjustable connection between spinal fixation devices such as spinal fixation rods and allows for adjustment in length or distance between adjacent spinal rod clamping members and provides independent rotational adjustment of the two spinal rod clamping members for individual and independent attachment thereof to adjacent spinal rods of a spinal rod assembly. The cross-connector has first and second connection members that are adjustable in length and rotation relative to one another. A first spinal rod clamping member is provided on an end of the first connection member and defines first and second arced jaws that are adapted to clamp onto a first spinal rod. A second spinal rod clamping member is provided on an end of the second connection member and defines first and second arced jaws that are adapted to clamp onto a second spinal rod. Both the first and second clamping members are rotatable relative to the connection arms and thus provide the rotational adjustment. The individual and independent rotational adjustment of the spinal rod clamping members allows the present cross-connector to adjust to variations in skew between adjacent spinal rods as well as provide the ability to attach to the adjacent spinal rods at various angles between the adjacent spinal rods.

22 Claims, 10 Drawing Sheets

U.S. PATENT DOCUMENTS

| | | |
|---|---|---|
| 6,736,775 B2 | 5/2004 | Phillips |
| 7,314,331 B1 | 1/2008 | Koros et al. |
| 7,553,279 B1 | 6/2009 | Phillips et al. |
| 7,666,210 B2 * | 2/2010 | Franck et al. ............ 606/250 |
| 7,744,632 B2 | 6/2010 | Usher |
| 7,749,163 B2 | 7/2010 | Mulac et al. |
| 2003/0114853 A1 | 6/2003 | Burgess et al. |
| 2005/0113831 A1 | 5/2005 | Franck et al. |
| 2005/0228377 A1 | 10/2005 | Chao et al. |
| 2006/0064093 A1 | 3/2006 | Thramann et al. |
| 2006/0206114 A1 | 9/2006 | Ensign et al. |
| 2006/0271045 A1 | 11/2006 | Hubbard et al. |
| 2007/0049932 A1 | 3/2007 | Richelsoph et al. |
| 2007/0233090 A1 | 10/2007 | Naifeh et al. |
| 2008/0086134 A1 | 4/2008 | Butler et al. |
| 2009/0228046 A1 | 9/2009 | Garamszegi |

* cited by examiner

SPINAL CROSS-CONNECTOR

RELATED APPLICATIONS

This patent application claims the benefit of and/or priority to U.S. Provisional Patent Application Ser. No. 60/959,338 filed Jul. 13, 2007, entitled "Spinal Cross-Connector" the entire contents of which is specifically incorporated herein by this reference.

BACKGROUND OF THE INVENTION

1. Field of the Invention

The present invention relates to spinal fixation devices and, in particular, to cross-connectors for connecting spinal fixation devices, such as spinal rods that are attached onto a patient's spine.

2. Background Information

There are many medical situations, because of disease, injury or deformity, where it is necessary to align and/or fix a desired relationship between adjacent vertebral bodies. In order to accomplish this goal, orthopedic spinal surgeons utilize spinal fixation devices to provide the desired relationship between adjacent vertebral bodies. Such spinal fixation devices typically include a spinal fixation element, such as a relatively rigid fixation rod, that is connected to adjacent vertebrae by attaching the rod to anchor devices implanted into the vertebrae.

Often, the spinal fixation rods are placed on opposite sides of the spinous process in a substantially parallel relationship. These spinal fixation rods may have pre-determined contours according to properties of the target implantation site. Once installed, the spinal fixation rods hold the vertebrae in a desired spatial relationship.

It may also be necessary in some circumstances to provide a spinal cross-connector at one or more points between the two spinal fixation rods in order to provide additional stability to the structure. Particularly, adjacent spinal fixation rod assemblies can be made more robust by using a cross-connector to bridge the pair of spinal rods.

While current spinal cross-connectors are effective, problems exist such as in mounting and maintaining the cross-connectors in a desired position and orientation with respect to the spinal rods. Other problems also exist with current cross-connectors such as sizing and locking issues.

Accordingly, there presently exists a need for an improved spinal cross-connector that can be easily installed and that securely mates and connects to spinal fixation devices such as spinal rods.

SUMMARY OF THE INVENTION

The present invention is a spinal cross-connector for connection between adjacent spinal rods. The spinal cross-connector is configured, operable and/or adapted to allow adjustment in length or distance between adjacent spinal rod clamping members (i.e. lateral adjustment of the cross-connector) and to allow individual and independent rotational adjustment of the two spinal rod clamping members (i.e. rotational adjustment of the cross-connector) for individual and independent attachment thereof to the adjacent spinal rods. The individual and independent rotational adjustment of the spinal rod clamping members allows the present cross-connector to adjust to variations in skew between adjacent spinal rods as well as provide the ability to attach to the adjacent spinal rods at various angles between the adjacent spinal rods.

The present cross-connector is characterized by first and second connection members or arms that are adjustably fixable in length relative to one another. The first connection member has a first spinal rod clamping member that is adapted to be connected to one spinal rod while the second connection member has a second spinal rod clamping member that is adapted to be connected to the other, adjacent spinal rod. Each clamping member is rotatable relative to the respective connection member and thus the respective spinal rod.

In one form, length adjustment of the cross-connector is achieved by the first connection member having an arm with a bore that slidably receives an arm of the second connection member. The first and second connection members thus slide toward and away from each other to provide length adjustment. Securement of the selected length is achieved by a set pin, threaded nut or the like.

In another form, length adjustment of the cross-connector is achieved by the first connection member having a slot that receives a fixation member which is attached to the second connection member. The first connection member is thus slidable relative to the fixation member and thus the second connection member. Securement of the selected length is achieved by the fixation member.

In one form, rotational adjustment of the cross-connector is achieved by the first connection member having a first rotatable spinal rod clamping member at one end thereof and the second connection member having a second rotatable spinal rod clamping member at one end thereof. The first and second spinal rod clamping members are rotatable and fixable individually and independent of the other such that individual and independent rotational adjustment of the spinal rod clamping members allows the present cross-connector to adjust to variations in skew between adjacent spinal rods as well as provide the ability to attach to the adjacent spinal rods at various angles between the adjacent spinal rods.

The present cross-connector provides easily adjustable sizing (length and rotation) between adjacent spinal rods.

The present cross-connector also provides easy in situ sizing and adjustability.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

A description of the features, functions and/or configuration of the components depicted in the various figures will now be presented. It should be appreciated that not all of the features of the components of the figures are necessarily described. Some of these non-discussed features, if any, as well as discussed features are inherent from the figures. Other non discussed features may be inherent in component geometry and/or configuration.

DETAILED DESCRIPTION OF AN EMBODIMENT OF THE INVENTION

Referring to FIGS. 1-5 there is depicted an exemplary embodiment of a spinal or spinal rod cross connector generally designated 10 (collectively, cross-connector 10) fashioned in accordance with the principles of the present invention. The cross-connector 10 is made from a biocompatible material such as titanium or stainless steel. However, other biocompatible material, materials or compounds may be used.

The cross-connector 10 is configured, operable and/or adapted to allow adjustment in length or distance between adjacent spinal rod connectors (i.e. lateral adjustment of the cross-connector) and to allow individual and independent rotational adjustment of the two spinal rod connectors (i.e. rotational adjustment of the cross-connector) for individual and independent attachment thereof to the adjacent spinal rods. The individual and independent rotational adjustment of the spinal rod connectors allows the present cross-connector 10 to adjust to variations in skew between adjacent spinal rods as well as provide the ability to attach to the adjacent spinal rods at various angles between the adjacent spinal rods.

Figure 10:
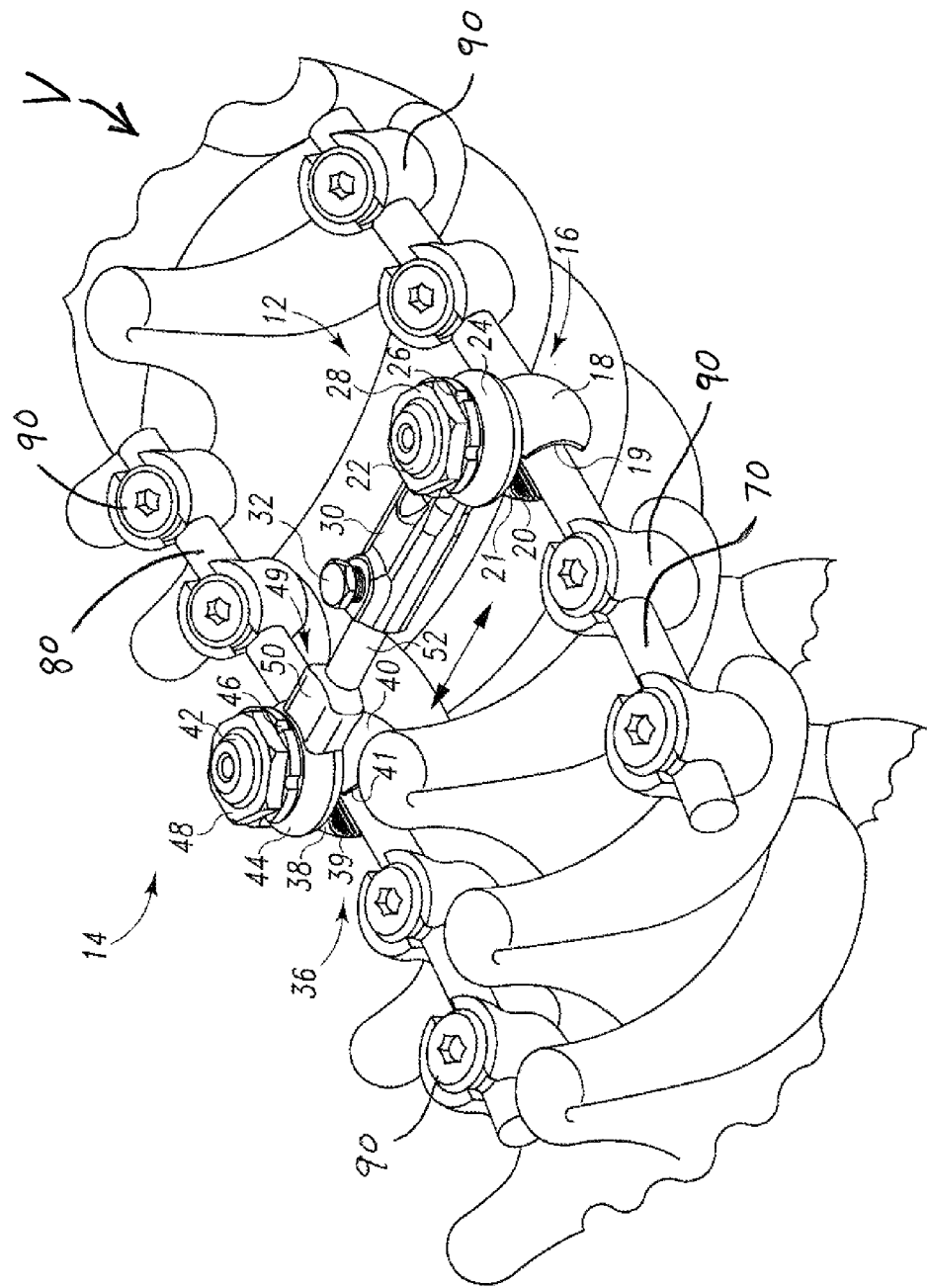
FIG. 10 is a top perspective view of a portion of a human spine having a spinal rod system attached thereto with one embodiment of the present spinal rod cross-connector attached to the spinal rod system.

The cross-connector 10 has a first spinal rod connector, connection member or arm 12 and a second spinal rod connector, connection member or arm 14 that are each adapted, configured and/or operable to connect to or clamp on to respective spinal rods (see FIG. 10). The cross-connector 10 is longitudinally adjustable as represented by the horizontal, double-headed arrow such that the span between the spinal rods is adjustable. Particularly, the first and second connection members 12, 14 are adjustable relative to one another in the direction of and as illustrated by the said horizontal, double-headed arrow. The connection members 12 and 14 are also rotatably adjustable with respect to one another.

The first connection member 12 has a first spinal rod clamp, clamping or attachment member 16 having first and second arced jaws or members 18 and 20. The first jaw 18 includes teeth 19 on its inner arced surface. The second jaw 20 also includes teeth 21 on its inner arced surface. The first and second jaws 18, 20 are thus adapted, configured and/or operable to extend about a spinal rod with the teeth 19, 21 of the respective jaws 18, 20 holding onto the spinal rod.

An upper portion of the first and second jaws 18, 20 extend through a generally annular collar 24 of the first connection member 12 and terminate in a threaded shaft 22. As represented by the arced, double-headed arrow of FIGS. 3 and 4, the jaws 18 and 20 are rotatable about the collar 24. This allows the clamping member 16 to swivel about the spinal rod. The threaded shaft 22 of the clamping member 16 extends through a generally annular insert 26 that is positioned axially above the collar 24. In one form, the insert 26 has a ball end that mates to a receiving ball socket of the collar 24. The interfacing between the ball end and ball socket provides rotational adjustability within the plane shown in FIG. 2 and the plane shown in FIG. 5. A threaded nut 28 is received onto the threaded shaft 22. As the nut 28 is received onto the shaft 22, the insert 26 is pressed against the collar 24 so as to fix the rotational orientation of the jaws 18, 20 relative to the collar 24. The nut 28 also fixates the clamping member 16 onto the rod. Prior to tightening of the nut 28, the clamping member 16 can be easily placed onto or removed from the rod and/or re-positioned along the axis of the rod.

The second connection member 14 has a second spinal rod clamp, clamping or attachment member 36 having first and second arced jaws or members 38 and 40. The first jaw 38 includes teeth 39 on its inner arced surface. The second jaw 40 also includes teeth 41 on its inner arced surface. The first and second jaws 38, 40 are thus adapted, configured and/or operable to extend about a spinal rod with the teeth 39, 41 of the respective jaws 38, 40 holding onto the spinal rod.

An upper portion of the first and second jaws 38, 40 extend through a generally annular collar 44 of the second connection member 14 and terminate in a threaded shaft 42. As represented by the arced, double-headed arrow of FIGS. 3 and 4, the jaws 38 and 40 are rotatable about the collar 44. This allows the clamping member 36 to swivel about the spinal rod. The threaded shaft 42 of the clamping member 36 extends through a generally annular insert 46 that is positioned axially above the collar 44. In one form, the generally annular insert 46 has a ball end that mates to a receiving ball socket of the collar 44. The interfacing between the ball end and ball socket provides rotational adjustability within the plane shown in FIG. 2 and the within the plane shown in FIG. 5. A threaded nut 48 is received onto the threaded shaft 42. As the nut 48 is received onto the shaft 42, the insert 46 is pressed against the collar 44 so as to fix the rotational orientation of the jaws 38, 40 relative to the collar 44. The nut 48 also fixates the clamping member 36 onto the rod. Prior to tightening of the nut 48, the clamping member 36 can be easily placed onto or removed from the rod and/or re-positioned along the axis of the rod.

The first connection member 12 includes an arm 30 that radially extends from the collar 24. The arm 30 is generally rectangular in cross section and has a generally round longitudinal bore 31 therethrough (see FIG. 4) with an opening thereof distal the collar 24. The second connection member 14 includes an arm 49 that radially extends from the collar 44. The arm 49 has a first arm portion 50 of a first size that is proximate the collar 44 with a generally rectangular cross section. The arm 49 also has a second arm portion 52 of a second size and of a generally circular cross section that axially extends from the first arm portion 50. The second size of the second arm portion 52 is smaller than the first size of the first arm portion 50. The second arm portion 52 is sized for reception in the bore 31 of the arm 30 of the first connection member 12. Particularly, the second arm portion 52 is received in the bore 31 of the first connection member 12 to provide the longitudinal or length adjustment as well as the rotational adjustment of the present cross-connector 10.

Figure 1:
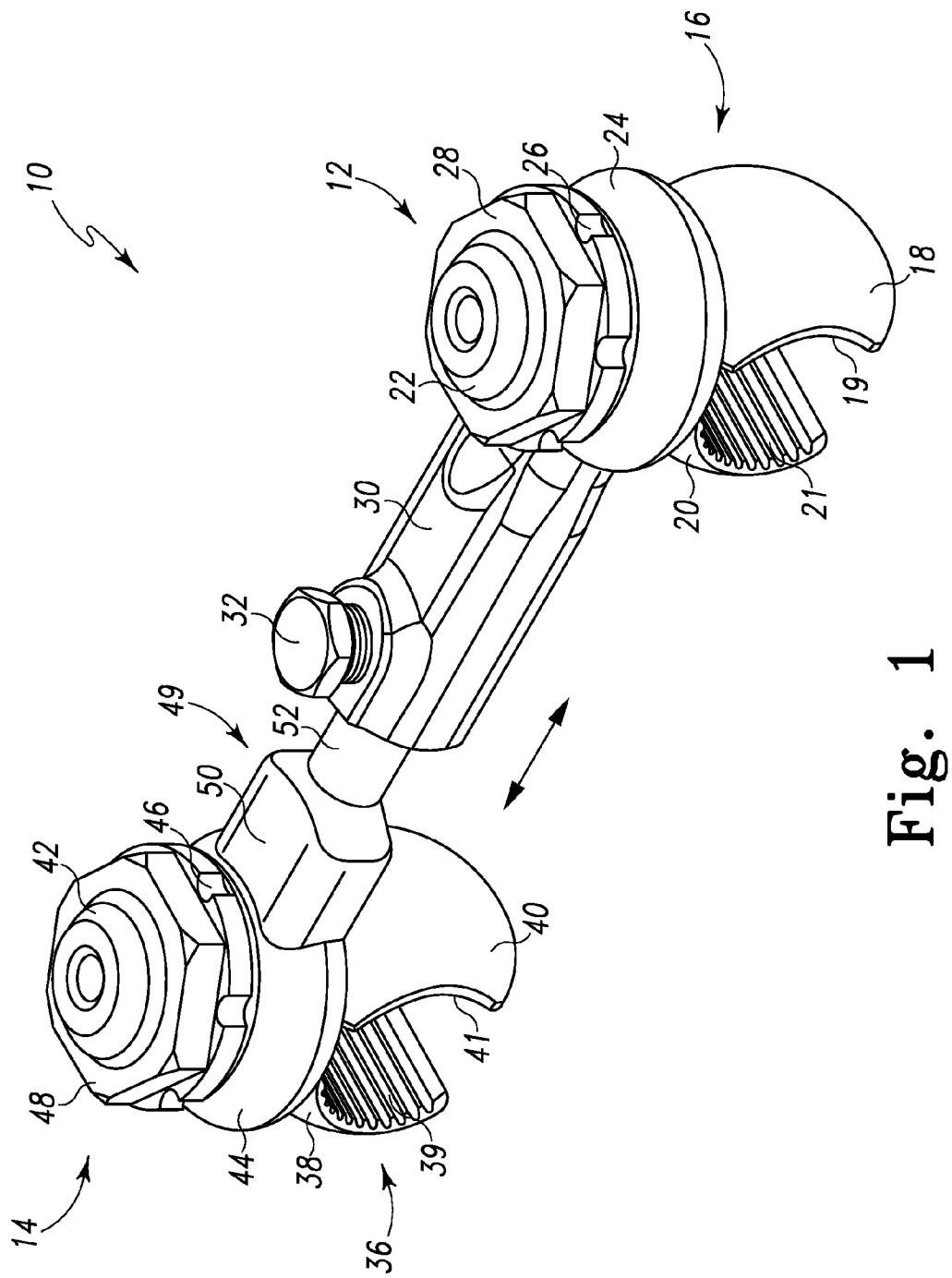
FIG. 1 is a perspective view of an exemplary spinal rod cross-connector fashioned in accordance with the present principles.
Figure 2:
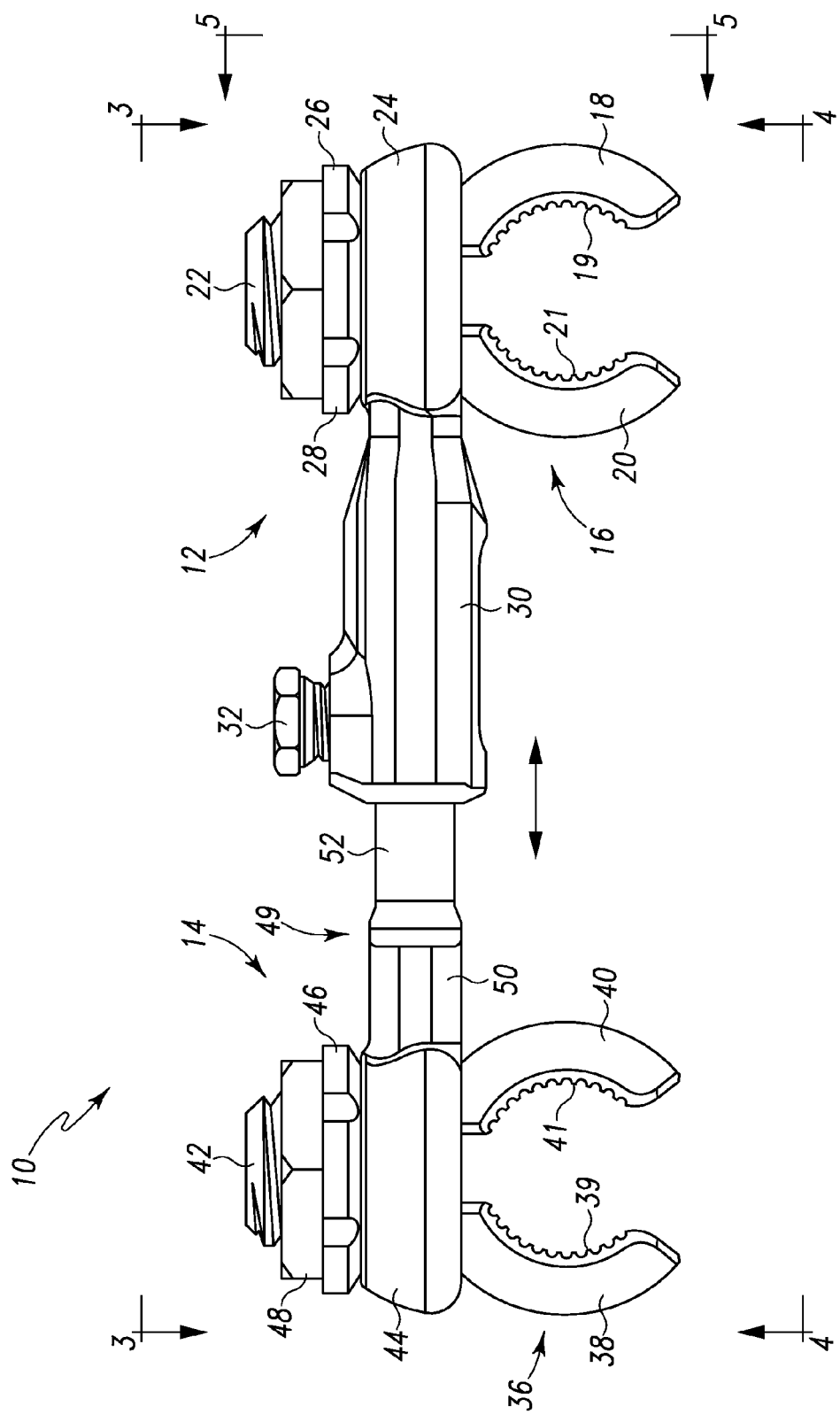
FIG. 2 is a side view of the spinal rod cross-connector of FIG. 1.
Figure 3:
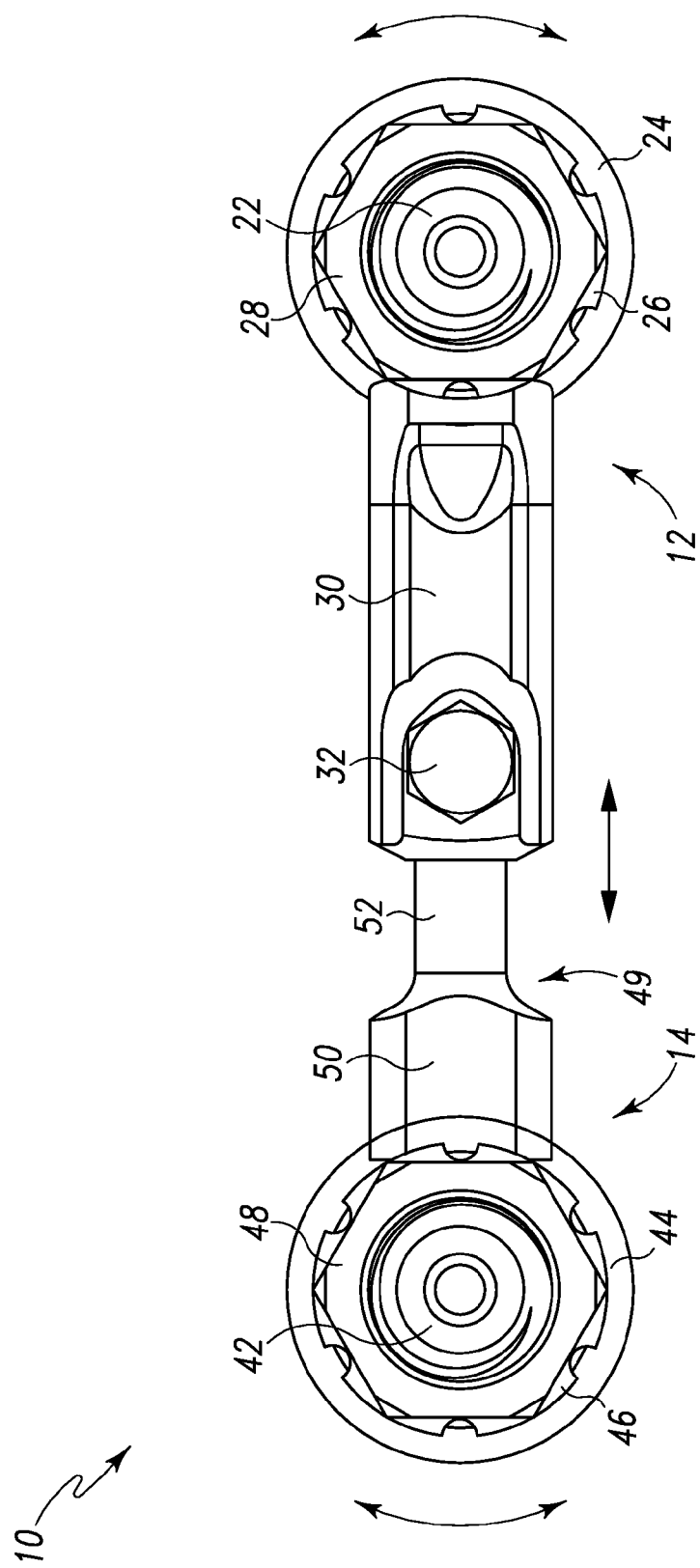
FIG. 3 is a top view of the spinal rod cross-connector of FIG. 1 taken along line 3-3 of FIG. 2.
Figure 4:
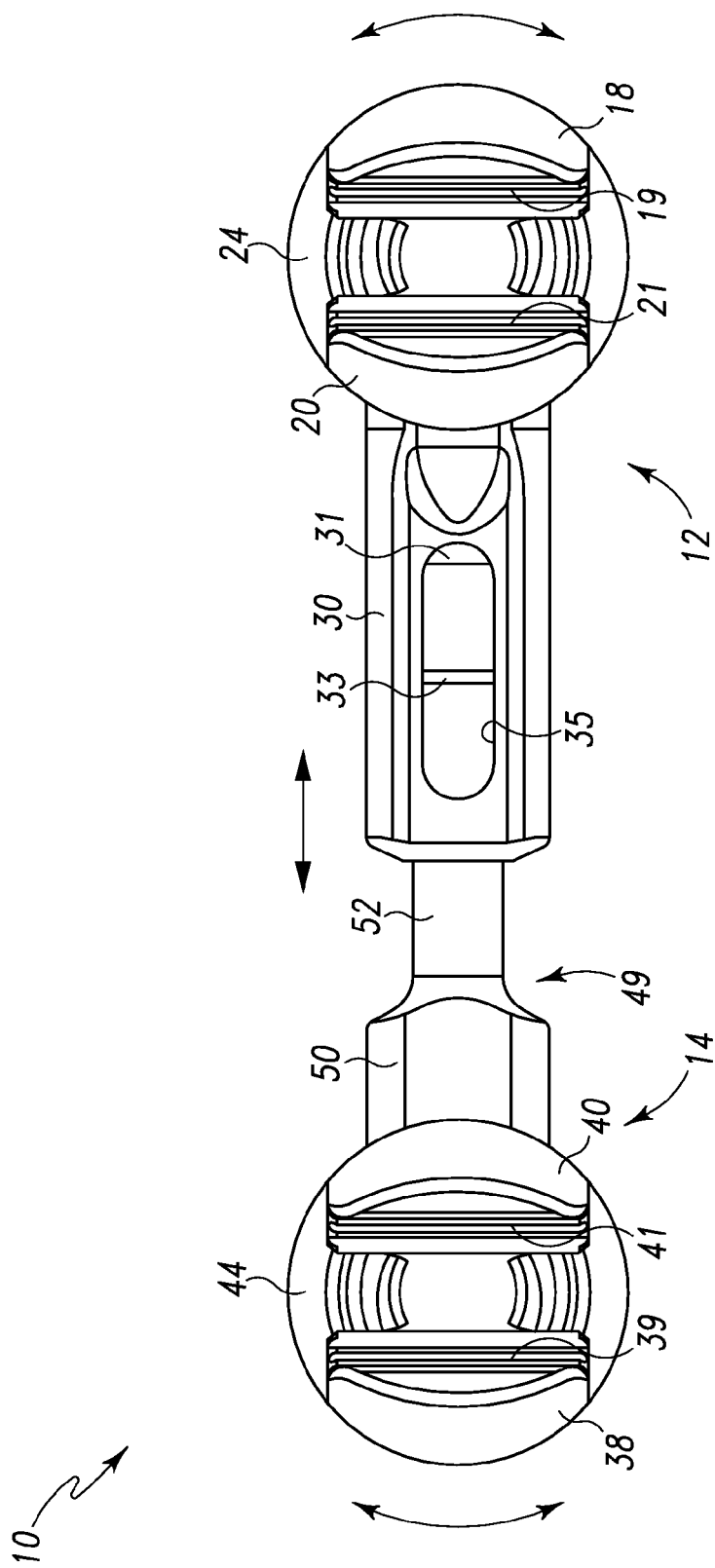
FIG. 4 is a bottom view of the spinal rod cross-connector of FIG. 1 taken along line 4-4 of FIG. 2.
Figure 5:
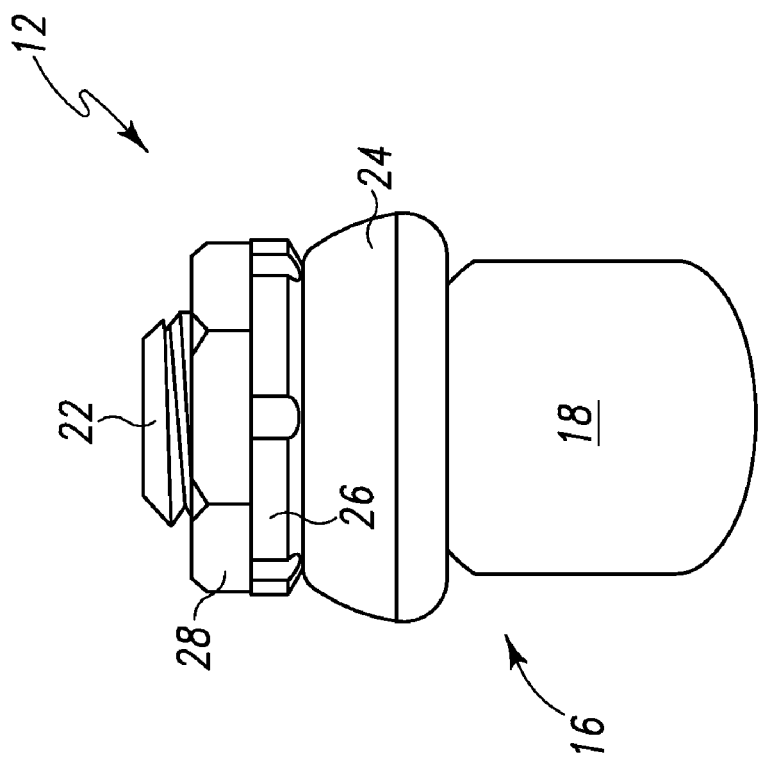
FIG. 5 is a side view of the spinal rod cross-connector of FIG. 1 taken along line 5-5 of FIG. 5.

The arm 30 of the first connection member 12 has a hex-head threaded screw 32 that extends into the bore 31. The threaded screw 32 fixes the position of the second arm portion 52 and thus the second connection member 14 relative to the first connection member 12. As best seen in FIG. 4, the second arm portion 52 has a line or demarcation 33 that can be seen through a window 35 of the arm 30. This allows positioning of the second arm portion 52 within the bore 31 of the arm 30. The second size of the first arm portion 50 of the arm 49 provides a stop defining a smallest length of the cross-connector 10.

The present cross-connector 10 thus provides simple length adjustment and easy rotational clamping to adjacent spinal rods. This allows the present cross-connector 10 to adjust to variations in spacing and skewness of adjacent spinal rods.

Figure 6:
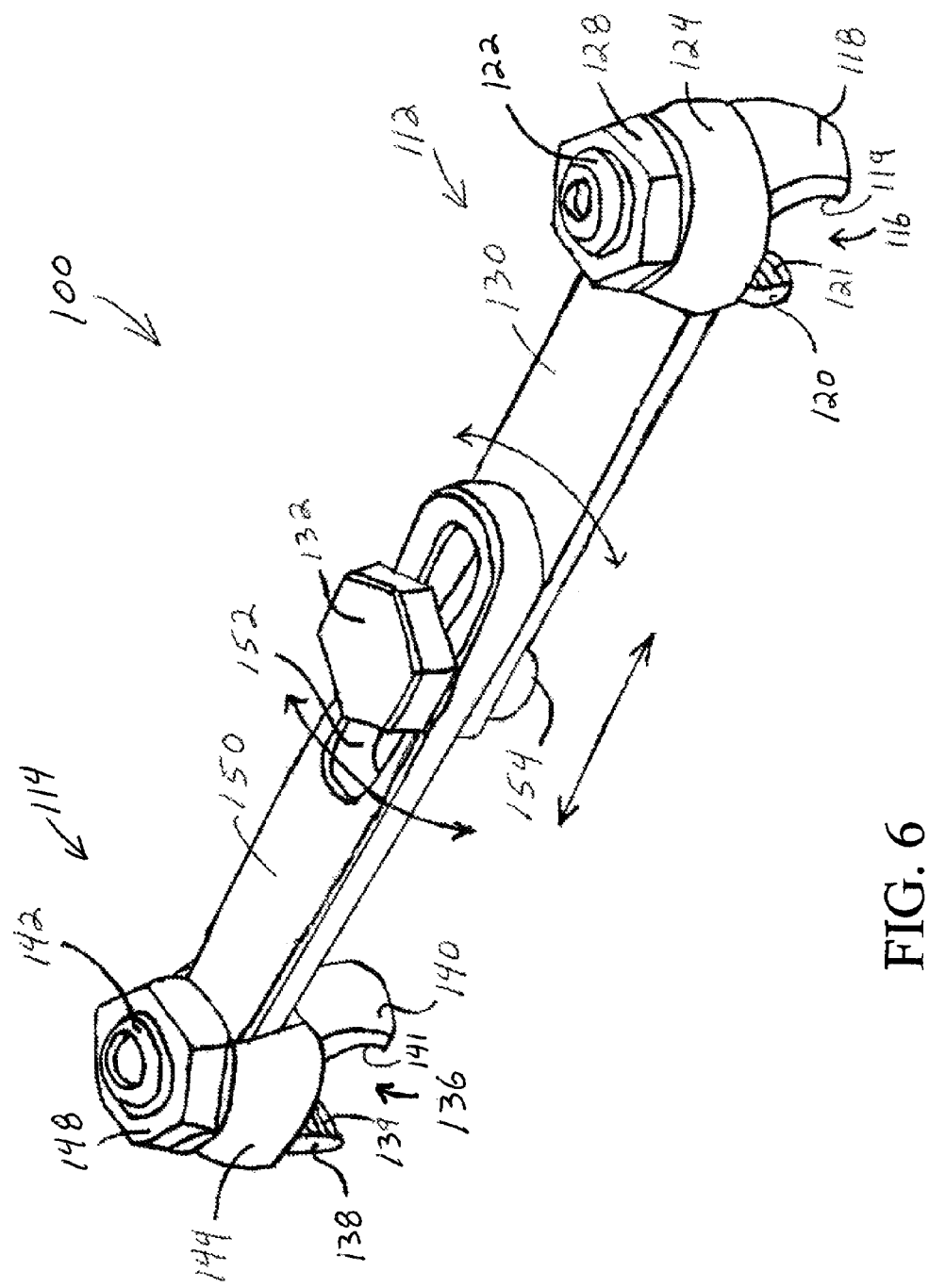
FIG. 6 is a perspective view of another exemplary embodiment of a spinal rod cross-connector fashioned in accordance with the present principles.
Figure 7:
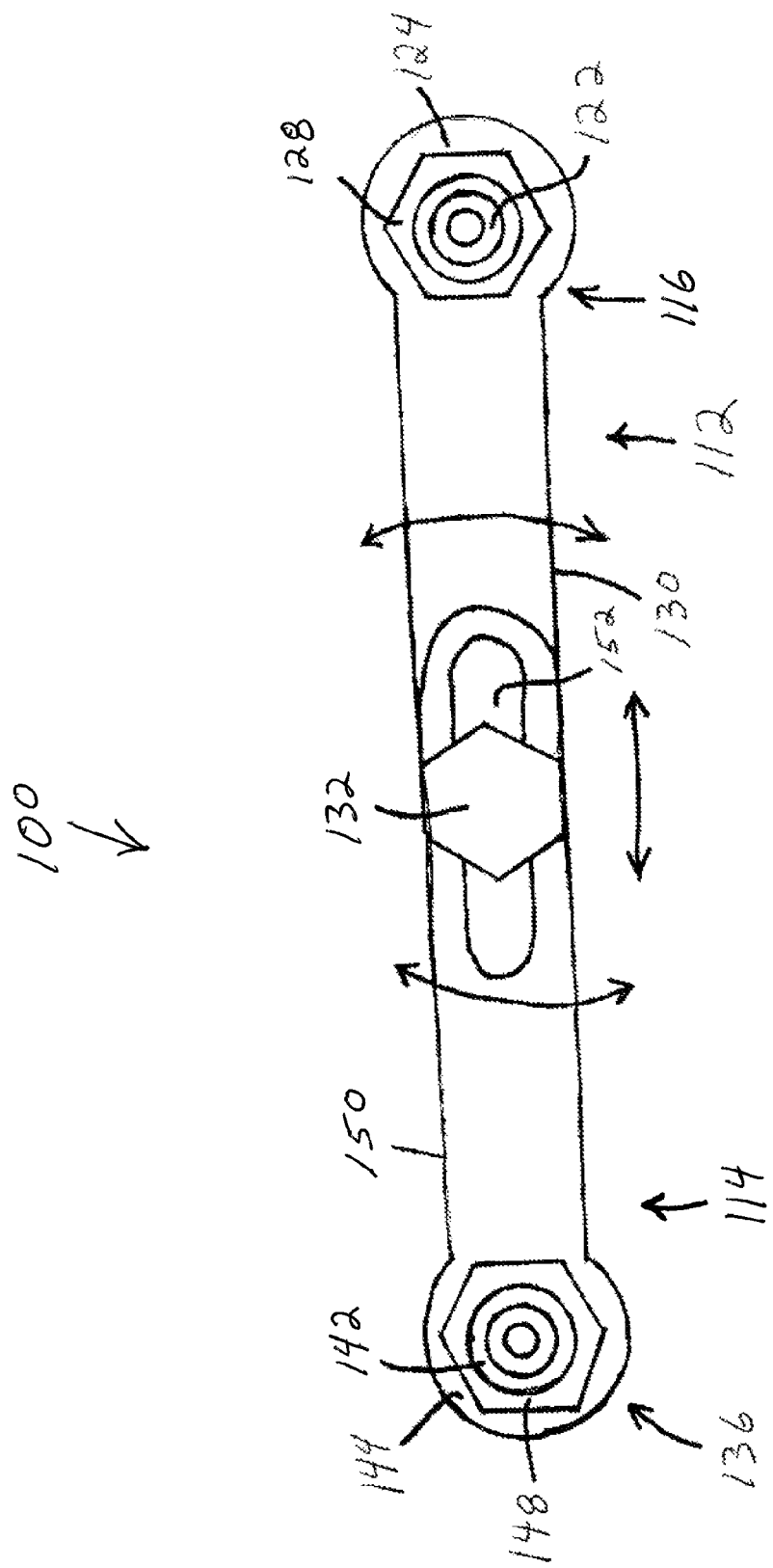
FIG. 7 is a top view of the spinal rod cross-connector of FIG. 6 taken along line 7-7 of FIG. 8.
Figure 8:
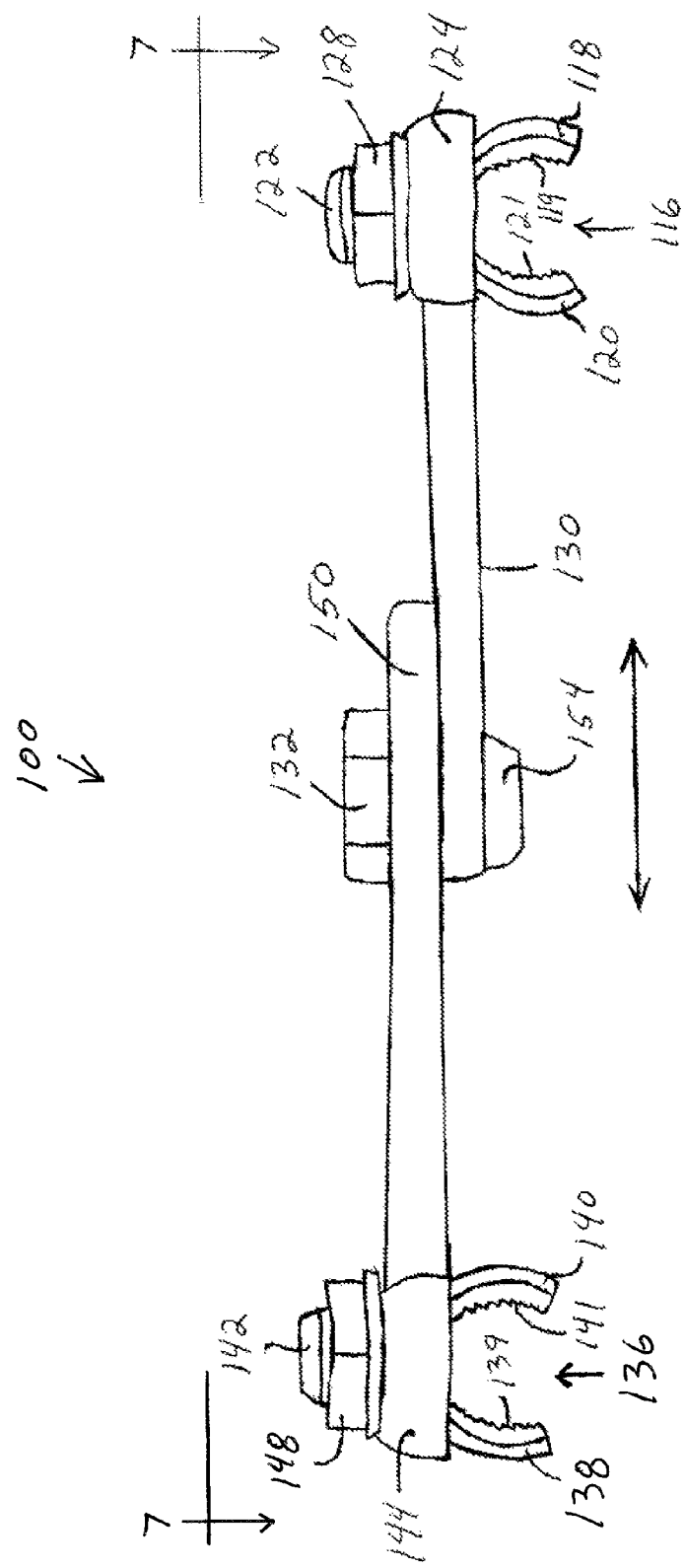
FIG. 8 is a side view of the spinal rod cross-connector of FIG. 6.

Referring now to FIGS. 6-8, there is depicted another exemplary embodiment of a spinal or spinal rod cross connector generally designated 100 (collectively, cross-connector 100) fashioned in accordance with the principles of the present invention. The cross-connector 100 is made from a biocompatible material such as titanium or stainless steel. However, other biocompatible material, materials or compounds may be used.

The cross-connector 100 is configured, operable and/or adapted to allow adjustment in length or distance between adjacent spinal rod connectors (i.e. lateral adjustment of the cross-connector) and to allow individual and independent rotational adjustment of the two spinal rod connectors (i.e. rotational adjustment of the cross-connector) for individual and independent attachment thereof to the adjacent spinal rods in like manner to the spinal rod cross-connector 10. The individual and independent rotational adjustment of the spinal rod connectors allows the present cross-connector 100 to adjust to variations in skew between adjacent spinal rods as well as provide the ability to attach to the adjacent spinal rods at various angles between the adjacent spinal rods.

The cross connector 100 has a first spinal rod connector, connection member or arm 112 and a second spinal rod connector, connection member or arm 114 that are each adapted, configured and/or operable to connect to or clamp on to respective spinal rods in like manner to spinal rod cross connector 10. The cross connector 100 is longitudinally adjustable as represented by the horizontal, double-headed arrow such that the span between the spinal rods is adjustable. Particularly, the first and second connection members 112, 114 are adjustable relative to one another in the direction of and as illustrated by the said horizontal, double-headed arrow. The connection members 112 and 114 are also rotatably adjustable with respect to one another.

The first connection member 112 is defined by an arm 130 with a first spinal rod clamp, clamping or attachment member 116 disposed at one end thereof. The first clamping member 116 has first and second arced jaws or members 118 and 120. The first jaw 118 includes teeth 119 on its inner arced surface. The second jaw 120 also includes teeth 121 on its inner arced surface. The first and second jaws 118, 120 are thus adapted, configured and/or operable to adjustably extend about a spinal rod with the teeth 119, 121 of the respective jaws 118, 120 holding onto the spinal rod.

An upper portion of the first and second jaws 118, 120 extend through a generally annular collar 124 of the first connection member 112 and terminate in a threaded shaft 122. The jaws 118 and 120 and threaded shaft 122 are thus rotatable about the collar 124. This allows the clamping member 116 to swivel about the spinal rod. A threaded nut 128 is received onto the threaded shaft 122. As the nut 128 is received onto the shaft 122, the jaws 118, 120 close around the spinal rod. The nut 128 fixates the clamping member 116 onto the spinal rod. Prior to tightening of the nut 128, the clamping member 116 can be easily placed onto or removed from the spinal rod and/or re-positioned along the longitudinal axis of the spinal rod.

The second connection member 114 is defined by an arm 150 with a second spinal rod clamp, clamping or attachment member 136 disposed at one end thereof. The second clamping member 136 has first and second arced jaws or members 138 and 140. The first jaw 138 includes teeth 139 on its inner arced surface. The second jaw 140 also includes teeth 141 on its inner arced surface. The first and second jaws 138, 140 are thus adapted, configured and/or operable to adjustably extend about a spinal rod with the teeth 139, 141 of the respective jaws 138, 140 holding onto the spinal rod.

An upper portion of the first and second jaws 138, 140 extend through a generally annular collar 144 of the second connection member 114 and terminate in a threaded shaft 142. The jaws 138 and 140 and threaded shaft 142 are thus rotatable about the collar 144. This allows the clamping member 136 to swivel relative to the spinal rod. A threaded nut 148 is received onto the threaded shaft 142. As the nut 148 is received onto the shaft 142, the jaws 138, 140 close around the spinal rod. The nut 148 fixates the clamping member 136 onto the spinal rod. Prior to tightening of the nut 148, the clamping member 136 can be easily placed onto or removed from the spinal rod and/or re-positioned along the longitudinal axis of the spinal rod.

The arm 130 of the first connection member 114 extends radially from the collar 124. The arm 130 is generally rectangular in cross section and has a bore therethrough (not seen) on an end thereof distal the collar 124. The arm 150 of the second connection member 114 extends radially from the collar 144. The arm 150 has a longitudinal slot 152 on an end thereof distal the collar 144. The fixation member 132 extends through the slot 152 and allows the connection members to pivot and slide relative thereto. This provides the longitudinal or length adjustment as well as the rotational adjustment of the present cross-connector 100.

The arm 30 of the first connection member 12 has a hex-head threaded screw 32 that extends into the bore 31. The threaded screw 32 fixes the position of the second arm portion 52 and thus the second connection member 14 relative to the first connection member 12. As best seen in FIG. 4, the second arm portion 52 has a line or demarcation 33 that can be seen through a window 35 of the arm 30. This allows positioning of the second arm portion 52 within the bore 31 of the arm 30. The second size of the first arm portion 50 of the arm 49 provides a stop defining a smallest length of the cross connector 10. The present cross connector 100 thus provides simple length adjustment and easy rotational clamping to adjacent spinal rods. This allows the present cross-connector 100 to adjust to variations in spacing and skewness of adjacent spinal rods.

Figure 9:
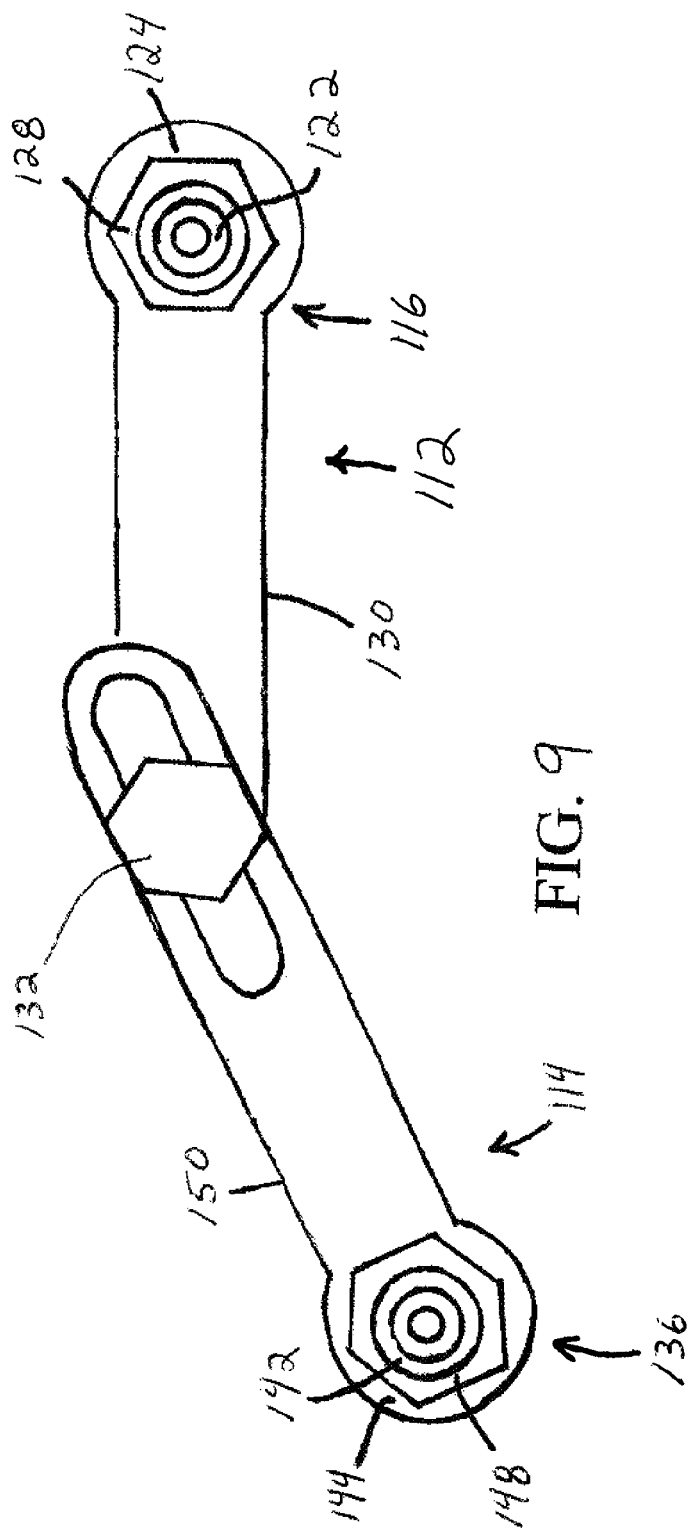
FIG. 9 is a top view of the spinal rod cross-connector of FIG. 6 in a skew position.

FIG. 9 shows the spinal rod cross-connector 100 in a bent position wherein the connection arms 130 and 150 are not co-axial but define an angle with respect to the fixation member 132. Various angles may be achieved.

With reference to FIG. 10, there is depicted the cross-connector 10 as attached to a spinal rod/spine screw assembly/system that is shown implanted onto adjacent vertebrae of a portion of a spine V. Particularly, the spinal cross-connector 10 is shown connected to two spinal rods 70, 80 of the spinal rod/spine screw assembly/system. The two spinal rods 70, 80 are each connected to a series of spine screws and spine screw heads/rod holders 90 attached to adjacent pedicles of the adjacent vertebrae. The present spinal rod cross-connector 10 is adjustable in length or span between the spinal rods 70, 80 (lateral adjustment). Additionally, each clamp 16, 36 rotates in the plane perpendicular to the adjustable span in order to provide adjustment of the clamps relative to the orientation of the spinal rods.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A spinal cross-connector comprising:
    a first connector;
    a second connector coupled to the first connector such that the first and second connectors define a span that is adjustable in length;
    a first spinal rod clamp attached to an end of the first connector by a first ball and socket joint and configured to attach onto a first spinal rod, the first spinal rod clamp rotatable relative to the end of the first connector, the first spinal rod clamp comprising a first pair of arced jaws that extend upward to form a first threaded shaft; and
    a second spinal rod clamp attached to an end of the second connector by a second ball and socket joint and configured to attach onto a second spinal rod, the second spinal rod clamp rotatable relative to the end of the second connector, the second spinal rod clamp comprising a second pair of arced jaws that extend upward to form a second threaded shaft.

2. The spinal cross-connector of claim 1, wherein the first spinal rod clamp is configured to releasably attach onto the first spinal rod, and the second spinal rod clamp is configured to releasably attach onto the second spinal rod.

3. The spinal cross-connector of claim 1, wherein the first spinal rod clamp rotates about an axis that is perpendicular to a longitudinal axis of the first connector, and the second spinal rod clamp rotates about an axis that is perpendicular to a longitudinal axis of the second connector.

4. The spinal cross-connector of claim 1, wherein the first pair of arced jaws adjustably attach to the first spinal rod, and the second pair of arced jaws adjustably attach to the second spinal rod.

5. The spinal cross-connector of claim 4, wherein the first and second arced pairs of jaws are each configured for radial size adjustment.

6. The spinal cross-connector of claim 1, wherein the first connector is slidably coupled to the second connector.

7. The spinal cross-connector of claim 6, wherein the first connector has an arm that is slidably received in a bore in the second connector.

8. The spinal cross-connector of claim 7, wherein the second connector has a cutout allowing viewing of position of a portion of the arm within the bore.

9. The spinal cross-connector of claim 6, wherein the first connector has a slot that is slidably received by a fixation member of the second connector.

10. The spinal cross-connector of claim 1, wherein rotation of the first spinal rod clamp is fixed by a first screw and nut adjustor, and rotation of the second spinal rod clamp is fixed by a second screw and nut adjustor.

11. The spinal cross-connector of claim 1, wherein the first ball and socket joint comprises a first insert forming a first ball portion, the first threaded shaft extending through the first insert; and
    wherein the second ball and socket joint comprises a second insert forming a second ball portion, the second threaded shaft extending through the second insert.

12. The spinal cross-connector of claim 1, wherein the first pair of arced jaws and the second pair of arced jaws both comprise a plurality of teeth on the inner surfaces thereof configured to engage the spinal rod.

13. The spinal cross-connector of claim 8, wherein the arm of the first connector comprises a transverse demarcation line indicating a position of the arm within the bore.

14. A spinal cross-connector comprising:
    an adjustable length span having a first end and a second end;
    a first spinal rod clamp disposed at the first end of the adjustable length span and configured to attach onto a first spinal rod, the first spinal rod clamp comprising a first pair of arced jaws that extend upward to form a first threaded shaft; and
    a second spinal rod clamp disposed at the second end of the adjustable length span and configured to attach onto a second spinal rod, the second spinal rod clamp comprising a second pair of arced jaws that extend upward to form a second threaded shaft;
    the first and second clamp members individually and independently rotationally adjustable relative to the adjustable length span for individual and independent attachment thereof to the first and second spinal rods;
    wherein each of the first and second spinal rod clamps are rotationally coupled to the adjustable length span by a ball and socket joint enabling rotation of the first and second spinal rod clamps relative to the adjustable length span.

15. The spinal cross-connector of claim 14, wherein the first and second spinal rod clamps rotate about an axis that is perpendicular to the adjustable length span.

16. The spinal cross-connector of claim 14, wherein the first pair of arced jaws adjustably attach to the first spinal rod, and the second pair of arced jaws adjustably attach to the second spinal rod.

17. The spinal cross-connector of claim 16, wherein the first and second arced pairs of jaws are each configured for radial size adjustment.

18. The spinal cross-connector of claim 14, wherein the adjustable length span is defined by a first connector that is slidably received on a second connector.

19. The spinal cross-connector of claim 18, wherein the first connector has an arm that is slidably received in a bore in the second connector.

20. The spinal cross-connector 18, wherein the first connector has a slot that is slidably and pivotally received by a fixation member of the second connector.

21. The spinal cross-connector of claim 19, wherein the second connector has a cutout allowing viewing of position of a portion of the arm within the bore.

22. The spinal cross-connector of claim 14, wherein rotation of the first spinal rod clamp is fixed by a first screw and nut adjustor, and rotation of the second spinal rod clamp is fixed by a second screw and nut adjustor.

* * * * *